United States Patent [19]

Boguslaski et al.

[11] 4,226,978

[45] Oct. 7, 1980

[54] β-GALACTOSYL-UMBELLIFERONE-LABELED AMINOGLYCOSIDE ANTIBIOTICS AND INTERMEDIATES IN THEIR PREPARATION

[75] Inventors: Robert C. Boguslaski; Robert J. Carrico; John F. Burd, all of Elkhart, Ind.

[73] Assignee: Miles Laboratories, Inc., Elkhart, Ind.

[21] Appl. No.: 886,094

[22] Filed: Mar. 13, 1978

[51] Int. Cl.$^2$ ................ C07H 15/22; C07H 17/04
[52] U.S. Cl. ........................................ 536/4; 424/2; 424/7; 435/7; 435/188; 536/17 R; 536/10
[58] Field of Search ............................ 536/4, 17 R

[56] References Cited

U.S. PATENT DOCUMENTS

| | | | |
|---|---|---|---|
| 3,652,536 | 3/1972 | Sebek et al. | 536/4 |
| 3,890,297 | 6/1975 | Dolak | 536/4 |
| 3,950,322 | 4/1976 | Thomas et al. | 536/4 |
| 3,960,835 | 6/1976 | Robertson | 536/4 |

*Primary Examiner*—Johnnie R. Brown
*Attorney, Agent, or Firm*—Andrew L. Klawitter

[57] ABSTRACT

β-Galactosyl-umbelliferone labeled aminoglycoside antibiotics, e.g., gentamicin, useful in homogeneous and heterogeneous specific binding assays for such antibiotics in liquid media such as serum. Also provided are a β-galactosyl-umbelliferone-carboxylic acid and salts thereof which are intermediates in a method of preparing the labeled antibiotics.

11 Claims, 10 Drawing Figures

DRUG IMMUNOASSAY

I. ENZYMATIC REACTION

LABELED DRUG $\xrightarrow{\text{enzyme}}$ FLUORESCENT PRODUCT

II. ANTIBODY BINDING REACTION

LABELED DRUG + ANTIBODY $\rightleftarrows$ LABELED DRUG-ANTIBODY COMPLEX $\xrightarrow{\text{enzyme}}$ NO REACTION

III. COMPETITIVE BINDING REACTION

LABELED DRUG + ANTIBODY + DRUG ASSAYED $\updownarrow$ LABELED DRUG-ANTIBODY COMPLEX + DRUG ASSAYED-ANTIBODY COMPLEX $\xrightarrow{\text{enzyme}}$ FLUORESCENT PRODUCT (REACTION RATE PROPORTIONAL TO DRUG ASSAYED)

FIG. 1

BETA-GALACTOSYL-UMBELLIFERONE-LABELED AMINOGLYCOSIDE ANTIBIOTICS AND INTERMEDIATES IN THEIR PREPARATION

BACKGROUND OF THE INVENTION

1. Field of the Invention

This invention relates to assay methods, and reagent means for use therein, of the homogeneous and heterogeneous specific binding type for determining qualitatively or quantitatively a ligand in a liquid medium. In particular, the invention relates to an improved nonradioisotopic binding assay employing a novel enzyme substrate label.

2. Description of the Prior Art

In German Offenlegungschriften Nos. 2,618,419 and 2,618,511, corresponding respectively to U.S. patent applications Ser. Nos. 667,982 and 667,996, both filed Mar. 18, 1976 both abandoned, and assigned to the present assignee, there are described homogeneous and heterogeneous specific binding assays employing an enzyme-cleavable substrate label. In exemplified embodiments there are disclosed the use of fluorogenic-labeled conjugates comprising umbelliferone or fluorescein coupled via an ester group to a ligand under assay or to a binding partner therefor. The amount of labeled conjugate in the bound-species and/or free-species resulting from the binding reaction system employed is determined by addition of an esterase which cleaves the ester group linking the umbelliferone or fluorescein residue to the ligand or binding partner to release the free fluorescent products, umbelliferone and fluorescein, respectively. The rate of fluorescence production, which follows the rate of release of the fluorescent product, is a function of the amount of ligand in the liquid medium tested.

Performance of this assay depends upon the ability to determine the amount of labeled conjugate which results in either the bound-species or the free-species relative to the amount initially introduced. Where the measured character of the labeled conjugate in the bound-species is essentially indistinguishable from that in the free-species, the two species must be physically separated in order to complete the assay. This type of binding assay follows what is conventionally known as a "heterogeneous" format. On the other hand, where the measured character of the labeled conjugate in the two species is distinguishable, a "homogeneous" format may be followed if desired and the separation step avoided.

While the above described binding assays employing an enzyme-cleavable substrate label offer a generic, novel approach to the pertinent art, the application of the assays to the detection of ligands in certain types of liquid media using the ester linked labeled conjugate is restricted. For example, the ester based assay has been found to be inconvenient for the detection of ligands appearing in the milligram per liter concentration range in physiological fluids such as serum and plasma. It has been found in this situation that the fluid under assay may contain a high endogenous esterase activity and, independently, the ester linked conjugate may exhibit a significant instability as the result of background hydrolysis under the conditions of the assay, which are usually alkaline.

SUMMARY OF THE INVENTION

It has now been found that the specific binding assay employing an enzyme-cleavable substrate label is greatly improved by the use of the novel label component described herein in formation of the labeled conjugate. According to the previously described assay method, the liquid medium under assay for a particular ligand is combined with reagent means, including a conjugate having a label component and a binding component, to form a binding reaction system having a bound-species and a free-species of such labeled conjugate, the label component of the conjugate comprising an enzyme-substrate active portion and an indicator portion, whereby the conjugate is cleavable by an enzyme to produce a detectable indicator product. The resulting bound-species and/or the free-species is contacted with the cleaving enzyme and the resulting indicator product measured as a function of the presence or amount of the ligand to be determined in the liquid medium assayed.

The present improvement comprises employing as the label component of the conjugate, a residue of the formula:

$$G-D-R$$

wherein G is a glycone, D is a dye indicator moiety, and R is a linking group through which the dye indicator moiety is covalently bound to the binding component of the conjugate. The cleaving enzyme employed to monitor the label in the bound-species or free-species accordingly is one capable of cleaving the glycosidic linkage between the glycone and the dye indicator moiety. The most preferred glycone and dye indicator moiety for the labeled conjugate are, respectively, a β-galactosyl group and an umbelliferone residue. The assay is adaptable to the detection of any specifically bindable ligand and is particularly useful in the detection of haptens such as drugs, particularly the aminoglycoside antibiotics.

The presently improved assay method and means feature the advantages of involving a cleaving enzyme for which negligible, if any, endogenous activity is found in physiological fluids such as serum and plasma, and of employing a labeled conjugate wherein the cleavable linkage is very stable under assay conditions in the absence of enzyme. For these reasons the present invention offers a significantly more accurate and reproducible assay than that previously known in the art. Further, antibody-induced hydrolysis of the cleavable linkage, which hydrolysis is sometimes found using the ester-linked labeled conjugates, is absent using the present glycosidic-linked conjugates. Even further, the reagents necessary for performing the assay generally exhibit greater stability, particularly the labeled conjugate, than prior reagents. The glycosidase enzymes involved in the present invention generally are stable over long storage periods and in dilute solutions.

BRIEF DESCRIPTION OF THE DRAWINGS

FIG. 1 is a schematic representation of the basic principles of a specific binding assay employing an enzyme-cleavable substrate label as applied to the immunoassay determination of a drug wherein the cleaved product is fluorescent.

DESCRIPTION OF THE PREFERRED EMBODIMENTS

Figure 2:
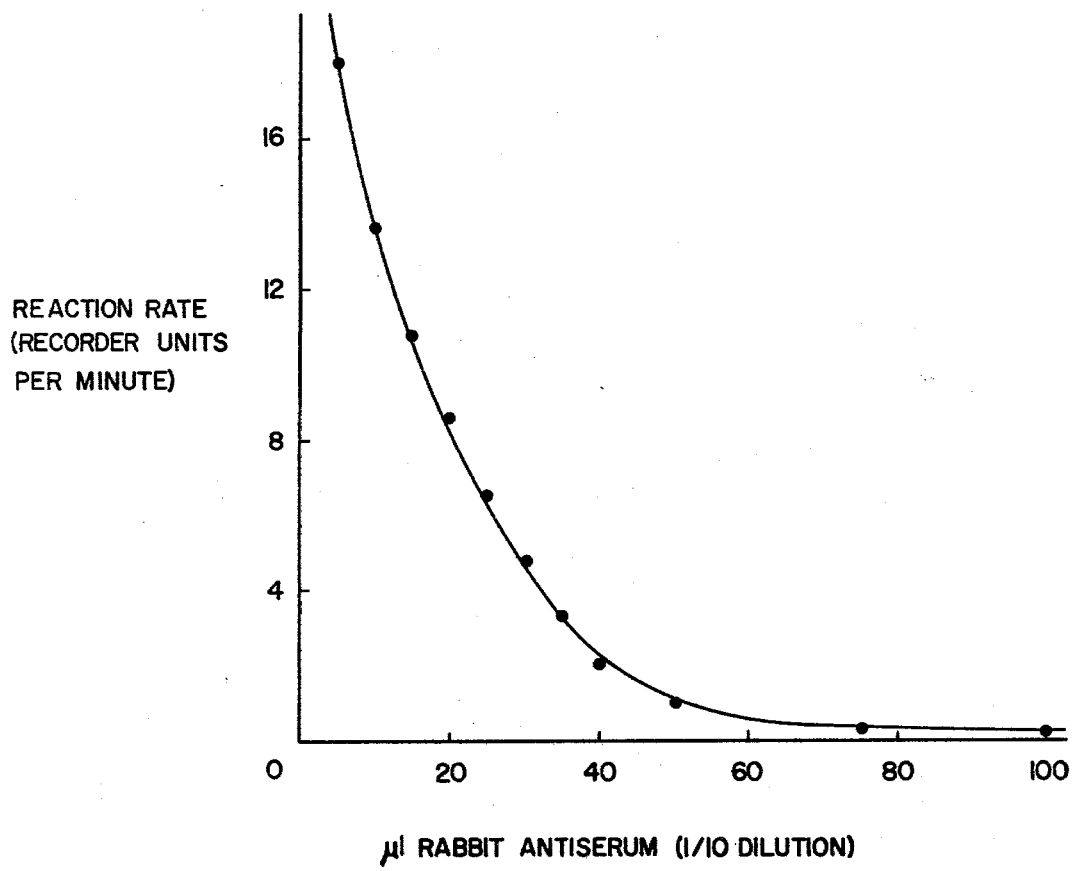
FIG. 2 is a graphical representation of the effect of increasing antibody concentration on the rate of release of cleaved product from a labeled conjugate for use in an assay for gentamicin as described in Example 1.

In the context of this disclosure, the following terms shall be defined as follows: "ligand" is the substance, or class of related substances, whose presence or the amount thereof in a liquid medium is to be determined; "specific binding partner of the ligand" is any substance, or class of substances, which has a specific binding affinity for the ligand to the exclusion of other substances; "specific binding analog of the ligand" is any substance, or class of substances, which behaves essentially the same as the ligand with respect to the binding affinity of the specific binding partner for the ligand; "monitoring reaction" is the reaction in which the glycosidic linkage in the labeled conjugate is cleaved enzymatically to release a detectable indicator product; "lower alkyl" is an alkyl group comprising from 1 to 6 carbon atoms, inclusive, such as methyl, ethyl, isopropyl, and hexyl.

LABEL RESIDUE

In the novel label residue of the present invention, the glycone may be any group which constitutes the carbohydrate portion of a glycoside. In general, therefore, the glycone is a sugar residue bound through an acetal linkage to the dye indicator moiety in the labeled conjugate. The sugar residue may be selected from residues of monosaccharides, including the aldo-, keto-, deoxy-, and derivatized forms of the trioses, tetroses, pentoses, hexoses and heptoses in their D- or L-stereoisomeric forms; oligosaccharides, such as disaccharides and trisaccharides; and polysaccharides. Where the acetal linkage to the dye indicator moiety is adjacent to an anomeric carbon in the glycone, both the α- and β- stereoconfigurations may be used. It is preferred that the glycone be a monosaccharide such as a pentose, e.g., ribose, arabinose, xylose, and lyxose, with hexoses being particularly preferred, e.g., galactose, glucose, mannose, and gulose. Derivatized monosaccharide residues which may be used include, without limitation, amino-substituted sugars, e.g., glucosamine and galactosamine, O-acyl and O-methyl derivatives, and glucuronides. It is contemplated that oligo- and polysaccharides and their derivatives may be used as well, e.g., the disaccharide cellobiose.

The most preferred group from which the glycone is selected consists of galactosyl, particularly α- and β-D-galactosyl; glucosyl, particularly α- and β-D-glucosyl; N-acetyl-galactosaminyl, particularly N-acetyl-α- or N-acetyl-β-D-galactosaminyl; N-acetyl-glucosaminyl, particularly N-acetyl-α- and N-acetyl-β-glucosaminyl; glucuronyl, particularly β-D-glucuronyl; arabinosyl, particularly α-L-arabinosyl; fucosyl, particularly β-L-fucosyl; mannosyl, particularly α-D-mannosyl; and xylosyl, particularly β-D-xylosyl. The most preferred glycone is a β-galactosyl group.

DYE INDICATOR MOIETY

With regard to the dye indicator moiety in the novel label residue of the present invention, this moiety may comprise any constitutent, usually one containing an organic nucleus especially of aromatic character, couplable to the glycone through a glycosidic linkage and to the binding component of the labeled conjugate through a suitable linking group, such that upon cleavage of such glycoside linkage by an enzyme appropriate for the glycone, there results a detectable dye product distinguishable from the intact labeled conjugate. Preferably the dye indicator moiety is of a type such that the detectable dye product of the enzymatic cleavage is fluorometrically or colorimetrically active. The desired distinctive indicator property of the cleaved product is obtained, in general, by linking the glycone and the dye indicator moiety at a site on the nucleus of the latter such that the fluorogenic or chromogenic character of the cleaved dye product is distinct from that of the intact labeled conjugate. For example, the fluorogenic and chromogenic characters of many known aromatic dyes can be altered by modifying an aryl hydroxyl group. Such a group provides an available site for linkage to the glycone through a glycosidic linkage which upon enzymatic cleavage results in release of a dye product having a fluorogenic or chromogenic character similar to that of the aromatic dye before formation of the labeled conjugate. Usually the fluorescence spectrum of the dye indicator moiety in the labeled conjugate will be shifted from that of the aromatic dye itself. The cleavage reaction is shown schematically below wherein

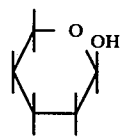

would represent the sugar precursor of the glycone with only the anomeric hydroxyl group specifically shown, A is an aryl nucleus, R is the linking group and L is the binding component of the labeled conjugate:

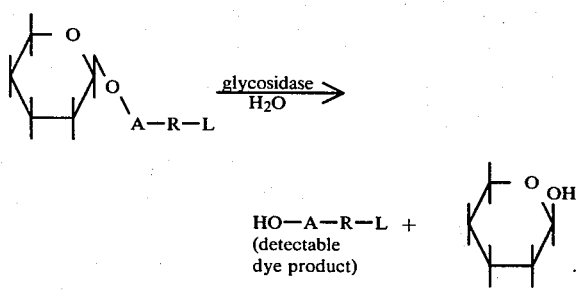

Examples of dyes useful for incorporation into the labeled conjugate of the present invention as the dye indicator moiety are umbelliferone, fluorescein, naphthol, indole, pyridol and resorufin, and active derivatives thereof. Following in Table 1 are representative labeled conjugates comprising residues of such dyes which are contemplated for use in the present invention. G(O)— represents the glycone terminating in a bridging oxygen atom which forms a part of the acetal linkage with the dye indicator moiety and —R—L represents a linking group and the linked binding component for the conjugate.

TABLE 1

| dye residue | structural formula |
|---|---|
| umbelliferone [wherein one of $R^1$ and $R^2$ is —R—L and the other is hydrogen or methyl] | G(O)—(structure with $R^1$, $R^2$) |
| fluorescein [wherein $R^2$ is hydroxyl or —(O)G] | G(O)—(fluorescein structure with $R^3$, L—R) |
| 3-indole | (indole structure with (O)G and R—L on N) |
| naphtol | (naphthalene structure with R—L and (O)G) |
| pyridol | (pyridine structure with (O)G and R—L) |
| resorufin | (resorufin structure with (O)G and R—L) |

Other variations of labeled conjugates based on the above listed dye residues are clearly evident. Various derivatives, particularly in the nature of aryl side chain derivatives, which retain sufficient ability to be coupled to the glycone and binding component and to exhibit appropriate fluorogenic or chromogenic character in the cleaved indicator product may be used in preparing labeled conjugates. Labeled conjugates which are prepared using such a substituted dye as starting material will possess substantially the same properties as the conjugates prepared from the above-listed dyes. Such conjugates will be recognized as equivalents and are exemplified by addition of one, two or more simple substituents to an available aromatic ring site, such substituents including without limitation lower alkyl, e.g., methyl, ethyl and butyl; halo, e.g., chloro and bromo; nitro; carboxyl; carbo lower alkoxy, e.g., carbomethoxy and carbethoxy; amino; mono- and di-lower alkylamino, e.g., methylamino, dimethylamino and methylethylamino; amido; hydroxyl; lower alkoxy, e.g., methoxy and ethoxy; and so forth.

LINKING GROUP

It will be recognized that there are many methods available for linking the binding component of the labeled conjugate, e.g., the ligand to be detected, a binding analog thereof, or a binding partner thereof, to the dye indicator moiety. The particular chemical character of the linking group will depend upon the nature of the respective available linking sites on the binding component and the dye indicator moiety. The important considerations in selecting the linking sites are (1) preservation of the ability of the linked binding component to participate effectively in the selected binding assay system and (2) preservation of the ability of the linked dye indicator moiety upon enzymatic cleavage to yield an effectively detectable product, in both cases, to the extent that a useful assay will result for the particular ligand under assay and for the particular concentrations or amounts in which such ligand is to be detected. Usually the linking group will comprise a chemical bond, usually a single, but sometimes a double bond, or a chain containing between 1 to 10, more commonly 1 to 6, carbon atoms and 0 to 5, more commonly 1 to 3, heteroatoms selected from nitrogen, oxygen, and sulfur.

Both the dye indicator moiety and the binding component, of course, will offer a great diversity of available functionalities for attachment of the linking group. Commonly the functionalities that can be expected to be available to the linking group are amino, usually primary amino; hydroxyl; halo, usually chloro or bromo; carboxylic acid; aldehyde; keto; isothiocyanate; isocyanate; and so forth. Accordingly, the chemical structure of the linking group itself will vary widely with its terminal groups depending on the functionalities available on the dye indicator moiety and the binding component and its overall length being a matter of choice within the basic constraint of maintaining the essential enzymatic substrate and binding component characters of the resulting conjugate. With regard to the length of the linking group in preparing a conjugate for use in a homogeneous assay format, it is usually desirable to use as short a group as possible without causing the resulting binding component in the conjugate to interfer significantly with the substrate activity of the conjugate. Where the binding component is of low molecular weight (e.g., a hapten of molecular weight between 100 and 1000), the linking group is preferably a chemical bond or a 1 to 3 atom chain such as carbonyl, amido, and the like. In other circumstances, such as where the binding component in the conjugate is of relatively high molecular weight, such as a polypeptide or protein (e.g., an antibody), a longer linking group is usually desirable to prevent steric hindrance of the substrate-active site of the conjugate. In these cases, the linking group will comprise usually 4 to 10 carbon atoms and 0 to 5 heteroatoms as previously discussed. Chains of any significantly greater length will tend to result in conjugates in which the binding component will tend to fold-back into the substrate-active site. With these considerations in mind, examples of linking groups are shown in Table 2. Particular examples of linking groups will be seen hereinafter and further variations will be readily recognized as being state-of-the-art.

TABLE 2

| | linking group | |
|---|---|---|
| dye label—indicator component | $\begin{bmatrix} -R^4-\overset{\overset{X}{\|}}{C}-R^5- \\ -R^4-\overset{\overset{X}{\|}}{C}-X-R^5- \\ -R^4-X-\overset{\overset{X}{\|}}{C}-R^5- \\ -R^4-X-\overset{\overset{X}{\|}}{C}-X-R^5- \\ -\overset{\overset{X}{\|}}{C}-R^4-\overset{\overset{X}{\|}}{C}- \\ -R^4-X-R^5- \\ -X-R^4- \\ -R^4-X- \\ -X-R^4-X- \end{bmatrix}$ | binding component | wherein X is imino, sulfur or, preferably, oxygen; and $R^4$ and $R^5$ are, independently, a bond or lower alkylene such as methylene, ethylene, butylene or hexylene.

The preferred dye indicator moiety is an umbelliferone residue which is bound directly to the glycone by an acetal linkage at the 7-position and bound to the binding component through a linking group at the 3 or 4-position, preferably the former. Especially useful are labeled conjugates comprising such an umbelliferone residue coupled to a β-galactosyl group as the glycone at the 7-position and to the binding component through the 3-position. Such conjugates are represented as:

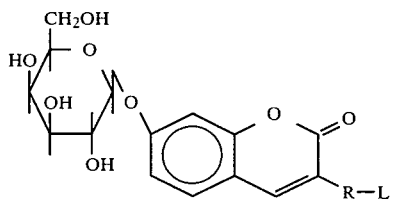

wherein R is a linking group and L is the binding component such as a hapten of molecular weight between 100 and 1000, or an analog thereof, particularly a drug or drug analog. Such conjugates find application in the detection of anticonvulsants such as diphenylhydantoin, phenobarbital, primidone, carbamazepine, ethosuximide, and sodium valproate; and particularly for detecting aminoglycoside antibiotics such as gentamicin, tobramycin, amikacin, kanamycin, sisomicin, and netilmicin; as well as others as described hereinafter. The linking group R is usually a single bond or a chain containing 1 to 10 carbon atoms and 0 to 5 heteroatoms selected from nitrogen, oxygen and sulfur. Where the binding component has an available primary amino group, the linking group may be carboxyl, forming an amide bond between the umbelliferone residue and such binding component.

The present assay may be applied to the detection of any ligand for which there is a specific binding partner. The ligand usually is a peptide, protein, carbohydrate, glycoprotein, steroid, or other organic molecule for which a specific binding partner exists in biological systems or can be synthesized. The ligand, in functional terms, is usually selected from the group consisting of antigens and antibodies thereto; haptens and antibodies thereto; and hormones, vitamins, metabolites and pharmacological agents, and their receptors and binding substances. Specific examples of ligands which may be detected using the present invention are hormones such as insulin, chorionic gonadotropin, thyroxine, liothyronine, and estriol; antigens and haptens such as ferritin, bradykinin, prostaglandins, and tumor specific antigens; vitamins such as biotin, vitamin $B_{12}$, folic acid, vitamin E, vitamin A, and ascorbic acid; metabolites such as 3',5' adenosine monophosphate and 3',5' guanosine monophosphate; pharmacological agents or drugs, particularly those described below; antibodies such as microsomal antibody and antibodies to hepatitis and allergens; and specific binding receptors such as thyroxine binding globulin, avidin, intrinsic factor, and transcobalamin. The present assay is particularly useful for the detection of haptens, and analogs thereof, of molecular weight between 100 and 1000, particularly drugs and their analogs, including the aminoglycoside antibiotics such as streptomycin, neomycin, and especially gentamicin, tobramycin, amikacin, kanamycin, sisomicin, and netilmicin; anticonvulsants such as diphenylhydantoin, phenobarbital, primidone, carbamazepine, ethosuximide, and sodium valproate; bronchodialators such as theophylline; cardiovascular agents such as quinidine and procainamide; drugs of abuse such as morphine, barbiturates and amphetamines; and tranquilizers such as valium and librium.

As stated previously, the present assay method may follow, in appropriate circumstances, either a homogeneous or a heterogeneous scheme.

HOMOGENEOUS SCHEMES

A homogeneous scheme, i.e., one which does not require a physical separation of the bound-species and the free-species, is available where reaction between the binding component of the labeled conjugate and a corresponding binding partner causes a measurable change, either in a positive or a negative sense, in the ability of the label component of the labeled conjugate to participate in the monitoring reaction, i.e., in the ability of the labeled conjugate to be cleaved enzymatically to release the detectable product. In such a case, the distribution of the label component between the bound-species and the free-species can be determined by adding the enzyme directly to the binding reaction mixture and measuring therein the activity of the substrate-active label component, i.e., the rate or total amount of detectable product that results, which preferably comprises measuring the rate of fluorescence or color production or the total amount thereof produced. Several manipulative schemes are available for carrying out a homogeneous assay with preference being given to the direct binding and competitive binding techniques.

Briefly, in the direct binding technique, a liquid medium suspected of containing the ligand to be detected, usually a compound of high molecular weight (e.g., an antibody) relative to a selected binding partner (e.g., an antigen or hapten), is contacted with the present labeled conjugate in which the binding component is the selected specific binding partner of the ligand, and thereafter any change in the substrate activity of the label component is assessed. In the competitive binding technique, primarily useful for the detection of a compound of low molecular weight (e.g., an antigen or hapten) relative to a selected binding partner (e.g., an antibody), the liquid medium is contacted with the selected specific binding partner of the ligand and with the present labeled conjugate in which the binding component is one of the ligand or a specific binding analog thereof, and thereafter any change in the substrate activity of the label component is assessed. In both techniques, the substrate activity of the label component is determined by contacting the liquid medium with an enzyme which can cleave the glycosidic linkage in the label component of the free-species form of the labeled conjugate and then measuring the rate or amount of detectable product which results. Qualitative determination of the ligand in the liquid medium involves comparing a characteristic, usually the rate, of the resulting reaction to that of the monitoring reaction in a liquid medium devoid of the ligand, any difference therebetween being an indication of the presence of such ligand in the liquid tested. Quantitative determination of the ligand in the liquid medium involves comparing a characteristic of the resulting reaction to that of the monitoring reaction in liquid media containing various known amounts of the ligand, e.g., a comparison to a standard curve.

A schematic representation of the principles of a competitive binding type of homogeneous immunoassay for a drug is shown in FIG. 1 of the drawing. As shown, the free labeled drug is acted upon by the enzyme to release a fluorescent product. However, upon addition of antibody to the drug, the action of the enzyme on the resulting labeled drug-antibody complex is inhibited, probably by steric hindrance. In the competitive binding reaction then, the ability of the enzyme to release the fluorescent product is dependent upon the ratio of labeled drug remaining free to that bound to antibody. Thus, the reaction rate of production of fluorescence is proportional to the amount of drug to be assayed which competes with labeled drug for antibody binding.

In general, when following a homogeneous assay scheme, the components of the specific binding reaction, i.e., the liquid medium suspected of containing the ligand, the labeled conjugate, and, in some systems, a specific binding partner of the ligand, may be combined in any amount, manner, and sequence, provided that the activity of the label component of the labeled conjugate is measurably altered when the liquid medium contains the ligand in an amount or concentration of significance to the purposes of the assay. Preferably, all of the components of the specific binding reaction are soluble in the liquid medium.

Known variations of the above briefly described homogeneous methods and further details concerning the specific techniques discussed are readily available in the literature, e.g., German OLS No. 2,618,511, corresponding to U.S. patent application Ser. No. 667,996, filed Mar. 18, 1976 and assigned to the present assignee.

HETEROGENEOUS SCHEMES

The use of the present novel substrate-active labels can also be applied to the conventional heterogeneous type assay schemes wherein the bound- and free-species of the labeled conjugate are separated and the quantity of label in one or the other is determined. The reagent means for performing such a heterogeneous assay may take on many different forms. In general, such means comprises three basic constituents, which are (1) the ligand to be detected, (2) a specific binding partner of the ligand, and (3) the labeled conjugate. The binding reaction constituents are combined simultaneously or in a series of additions, and with an appropriate incubation period or periods, the labeled conjugate becomes bound to its corresponding binding partners such that the extent of binding, i.e., the ratio of the amount of labeled conjugate bound to a binding partner (the "bound-species") to that unbound (the "free-species"), is a function of the amount of ligand present. The bound- and free-species are physically separated and the amount of label present in one thereof is compared to a negative control or standard results, e.g., a standard curve.

Various means of performing the separation step and of forming the binding reaction systems are available in the art. Separation may involve such conventional techniques as those involving what is commonly known as a solid-phase antibody or antigen, a second antibody, or a solid phase second antibody, as well as the use of immune complex precipitating agents and adsorbents, and so forth. Binding reaction systems that can be followed include the so-called competitive binding technique, the sequential saturation technique, the "sandwich" technique, and so forth. Further details concerning the various known heterogeneous systems are readily available in the literature, e.g., German OLS No. 2,618,419, corresponding to U.S. patent application Ser. No. 667,982, filed Mar. 18, 1976 and assigned to the present assignee.

It should be recognized that manipulative schemes involving other orders of addition and other binding reaction formats may be devised for carrying out homogeneous and heterogeneous specific binding assays without departing from the inventive concept embodied herein.

The liquid medium to be tested may be a naturally occurring or artificially formed liquid suspected of containing the ligand, and usually is a biological fluid or a liquid resulting from a dilution or other treatment thereof. Biological fluids which may be assayed following the present method include serum, plasma, urine, saliva, and amniotic, cerebral, and spinal fluids. Other materials such as solid matter, for example tissue, or gases may be assayed by reducing them to a liquid form such as by dissolution of the solid or gas in a liquid or by liquid extraction of the solid.

In general, in those instances where for purposes of a selected binding assay system the binding component in the labeled conjugate is the ligand or an analog thereof, the present labeled conjugate may be termed a glycone-dye-labeled ligand and may be represented by the formula:

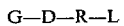

wherein G, D and R have their meanings as hereinabove and L is the ligand or analog thereof. Particularly useful conjugates for use in assays for haptens, especially those of molecular weight between 100 and 1000, are the β-galactosyl-umbelliferone-hapten conjugates of the formula:

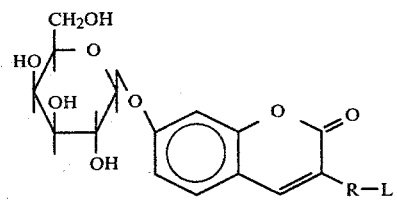

As stated hereinabove, the present invention finds particular application to the detection of aminoglycoside antibiotics, in particular, gentamicin, sisomicin, tobramycin, amikacin, kanamycin, and netilmicin. Particularly useful corresponding β-galactosyl-umbelliferone-ligand conjugates are represented by the formula below wherein the linking group between the umbelliferone residue and the aminoglycoside antibiotic is attached to the latter via a primary amino group of the isolated antibiotic. Since there are several available primary amino groups in each of the various antibiotics listed, one, two or more β-galactosyl-umbelliferone residues may be associated with one labeled antibiotic.

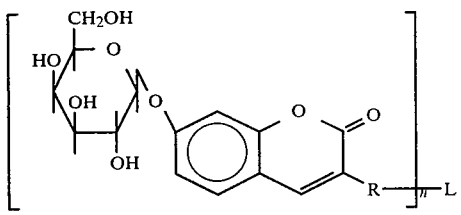

wherein R is a linking group as described hereinbefore terminating in an amino-linking group, preferably carbonyl; L is an aminoglycoside antibiotic selected from the group consisting of gentamicin, tobramycin, amikacin, kanamycin, sisomicin, and netilmicin, coupled by a covalent bond to the linking group R through a primary amino group therein; and n equals 1 to the total number of primary amino groups in the selected antibiotic, inclusive.

In preparing the above β-galactosyl-umbelliferone-aminoglycoside antibiotic conjugates wherein the linking group R is carbonyl, one first obtains the intermediate of the formula:

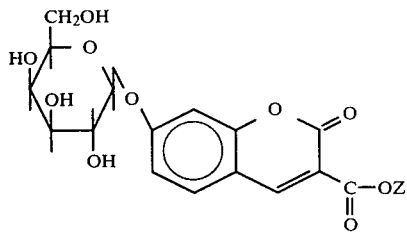

wherein Z is hydrogen or a suitable salt cation such as potassium or sodium, by reaction of 3-carboethyoxyumbelliferone and tetraacetyl-α-D-galactosyl bromide according to the method of Leaback, Clin. Chem. Acta 12:647(1965). Conjugation with the selected antibiotic then proceeds under suitable amide-bond producing conditions such as in the presence of acid and carbodiimide (cf. Table 3 below).

To perform an assay for an aminoglycoside antibiotic according to the present invention there may be used a labeled conjugate wherein the binding component is said antibiotic under assay or a binding analog thereof. Where an antibody is used as binding partner in the assay, such as in a homogeneous or heterogeneous competitive binding assay, it has been found that other aminoglycoside antibiotics may cross-react with the antibody for the antibiotic under assay. Thus such other antibiotics qualify as binding analogs and could be used to form the labeled conjugate. Further, the antibody qualifies as reagent for use in assays for the cross-reacting antibiotic. For example, in an assay for gentamicin it has been found that with appropriate antiserum the binding component in the labeled conjugate may be gentamicin itself or sisomicin which cross-reacts. Thus, gentamicin antiserum and a labeled sisomicin conjugate could be used in an assay for gentamicin. Specificity problems are not encountered in clinical situations because it would be known what antibiotic was administered and only one aminoglycoside antibiotic is administered at a time.

The present invention will now be illustrated, but is not intended to be limited, by the following examples.

EXAMPLE 1

Gentamicin Assays

A. Preparation of glycone-dye-drug conjugate

The reaction sequence for the preparation of the glycone-dye-drug conjugate is given in Table 3. 3-carboethoxy-7-hydroxycoumarin (II) was prepared by a Knoevenagel condensation of 2,4-dihydroxybenzaldehyde (Aldrich Chemical Co., Milwaukee, Wis., U.S.A.) with diethylmalonate in acetic acid, benzene, and piperidine as described in J. Am. Chem. Soc. 63:3452(1971). The potassium salt of β-[7-(3-carboxycoumarinoxy)]-D-galactoside (III) was prepared by the reaction of 3-carboethyoxy-7-hydroxycoumarin (II) and 2,3,4,6-tetraacetyl-α-D-galactosyl bromide (I, Sigma Chemical Co., St. Louis, Mo., U.S.A.) as described by Leaback for the preparation of methylumbelliferyl-β-D-galactoside in Clin. Chim. Acta 12:647(1965). The potassium salt of this compound was purified by chromatography on silica gel-60 (E. Merck, St. Louis, Mo., U.S.A.) with a gradient of n-butanol/methanol/water (4/2/1 by volume) and methanol/water (1/6). After recrystallization from acetone-water, the corrected melting point of the product was 258°–263° C. (decomp.). Analysis: calculated for $C_{16}H_{15}O_{10}K$: C 47.28%, H 3.73%, K 9.62%; found: C 47.30%, H 3.74%, K 9.34%. Optical rotation $[\alpha]D^{20} = -77.40$ (1 g.$H_2O$). NMR ($^2H_2O$), δ8.2(s, 1H), 7.6 (m,1H), 7.0 (m,2H), 5.1 (s,1H), and 4.0 (m,6H). Infrared analysis (KBr) indicated a carbon-oxygen double bond and a carbon-carbon double bond (1705 and 1620 $cm^{-1}$).

TABLE 3

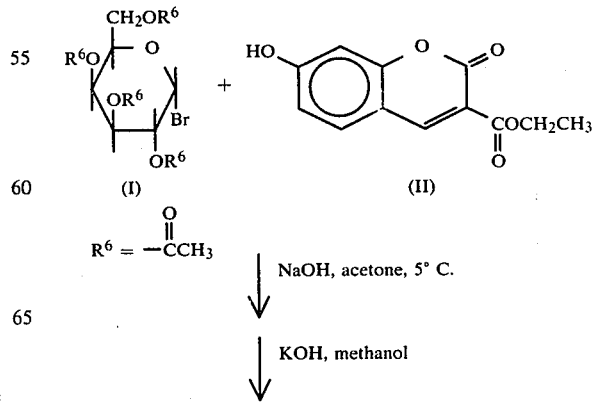

TABLE 3-continued

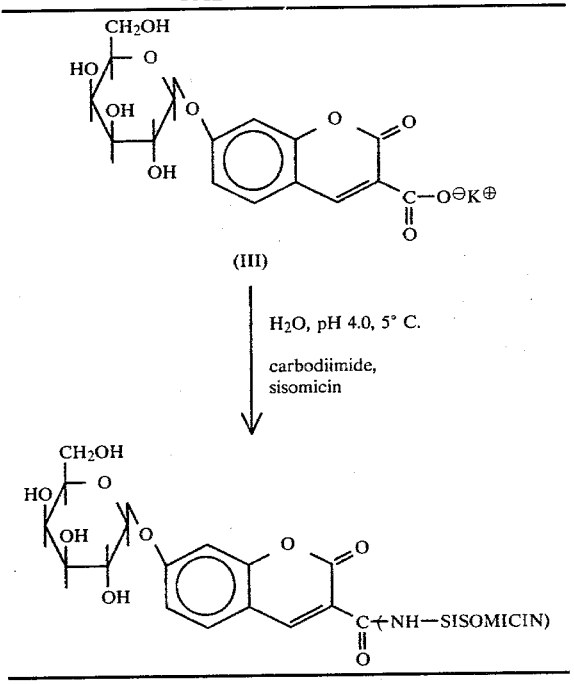

β-Galactosyl-umbelliferone-sisomicin (IV) was prepared by mixing 50 milligrams (mg) (117 μmol) of the potassium salt of β-[7-(3-carboxycoumarinoxy)]-D-galactoside (III) with 171 mg of sisomicin sulfate (223 μmol of sisomicin free base, Schering Corp., Bloomfield, N.J., U.S.A.) in 2 ml of water. The pH was adjusted to 3.8 by dropwise addition of 1 molar hydrochloric acid. The solution was cooled in an ice bath and 30 mg (150 μmol) of 1-ethyl-3-(3-dimethylaminopropyl)-carbodiimide hydrochloride (Pierce Chemical Co., Rockford, Ill., U.S.A.) was added. After 2 hours the mixture was chromatographed at 25° C. on a 2.5×50 centimeter (cm) column of CM-Sephadex C-25 (Pharmacia Laboratories, Inc., Piscataway, N.J. U.S.A.) 5.8 ml fractions were collected, and their absorbance was monitored at 345 nanometers (nm). The column was washed with 200 ml of 50 mmol/liter ammonium formate to elute unreacted β-[7-(3-carboxycoumarinoxy)]-D-galactoside (III). A linear gradient, formed with 400 ml of 50 mmol/liter and 400 ml of 1.8 mol/liter ammonium formate, was applied to the column. A peak of material absorbing at 345 nm eluted at approximately 1.4 mol/liter ammonium formate. After the gradient, the column was washed with 600 ml of 1.8 mol/liter ammonium formate. Three 345 nm absorbing peaks were eluted in this wash. Eluted unreacted sisomicin was well separated from the last 345 nm absorbing peak.

The carbodiimide-activated reaction leads to the formation of amide bonds between the carboxylic acid of β-[7-(3-carboxycoumarinoxy)]-galactoside and the primary amino groups of sisomicin. The major peak of β-galactosyl-umbelliferone-sisomicin (the last 345 nm absorbing peak) was used in the present studies. Ammonium formate was removed by lyophilization. Because the absorptivity of isolated labeled conjugate is currently unknown, the relative concentration is presented in terms of $A_{345}$ units. One $A_{345}$ unit is the quantity of material contained in 1 ml of a solution that has an absorbance of 1.0 at 345 nm when measured with a 1 cm light path.

B. Assay Procedure—Rate Assay

The principle of the assay is shown schematically in FIG. 1 of the drawings.

A reagent, prepared in 50 mmol/liter N,N-bis-(2-hydroxyethyl)-glycine (Bicine) buffer (pH 8.2, Nutritional Biochemicals Corp., Cleveland, Ohio, U.S.A.), contained β-galactosidase (25 ng protein/ml, Escherichia coli - derived enzyme, Grade IV, Sigma Chemical Co., St. Louis, Mo., U.S.A.) and antiserum to gentamicin (prepared as described in Nature New Biol. 239:214(1972) in an amount sufficient to decrease the reaction rate in the final reagent to 20 to 30% of the rate observed in the absence of antibody). One unit (U) of the enzyme was defined as that amount which hydrolyzed 1.0 μmole of β-nitrophenyl-β-D-galactoside per minute at pH 7.2 at 37° C. The enzyme preparation used had a specific activity of 745 U per milligram of protein.

To 2.0 ml aliquots of the reagent in a cuvette were added 1 μl aliquots of serum standards or unknown. After mixing, 5 μl of an aqueous solution of the labeled conjugate prepared in part A (0.125 $A_{345}$ units per ml) was added to each cuvette and the rate of increase in fluorescence was monitored in each for 2 to 3 minutes. All solutions were kept at 25° C., except the labeled conjugate which was kept in an ice bath.

C. Results—Rate Assay

The absorbance spectrum of the labeled conjugate, β-galactosyl-umbelliferone-sisomicin, showed an absorbance maximum at 345 nm. When the conjugate was hydrolyzed with bacterial β-galactosidase to remove the galactose moiety, the absorbance at 345 nm decreased and a new maximum appeared at 402 nm. The absorbance of the enzyme-treated conjugate was 1.46 times that of the untreated conjugate.

Analysis of the fluorescence spectrum of the conjugate revealed a similar shift in the maximum wavelength. Before enzyme treatment, the conjugate exhibited excitation and emission maxima at 350 and 394 nm, respectively. After hydrolysis with β-galactosidase, a 15-fold increase in fluorescense was observed, with new excitation and emission maxima of 409 and 445 nm, respectively. Hence, under the conditions of the fluorescent assay (excitation and emission wavelengths of 400 and 453) the unreacted conjugate contributed negligible fluorescence. For all of the aminoglycoside antibiotic assays reported herein, the excitation and emission wavelengths used in the fluorometric measurements were approximately 400 and 450 nm, respectively.

The effect of antiserum to gentamicin on the ability of the labeled conjugate to function as a substrate for β-galactosidase was examined. Various amounts of antiserum were added to 2.0 ml of buffered β-galactosidase. The labeled conjugate was added and the reaction rate determined using an Aminco-Bowman Spectrofluorometer connected to a strip-chart recorder. Reaction rats are expressed in terms of recorder units/minute. As the amount of antiserum increased, the reaction rate decreased as shown in FIG. 2 of the drawings. Based upon this experiment, an amount of antiserum sufficient to inhibit the reaction rate by 70 to 80% was chosen for the competitive binding reactions. The reaction between the antibody and the conjugate appeared to be complete in the time required for mixing the reagents, because incubation of the conjugate with the antibody before adding enzyme did not alter the results.

Figure 3:
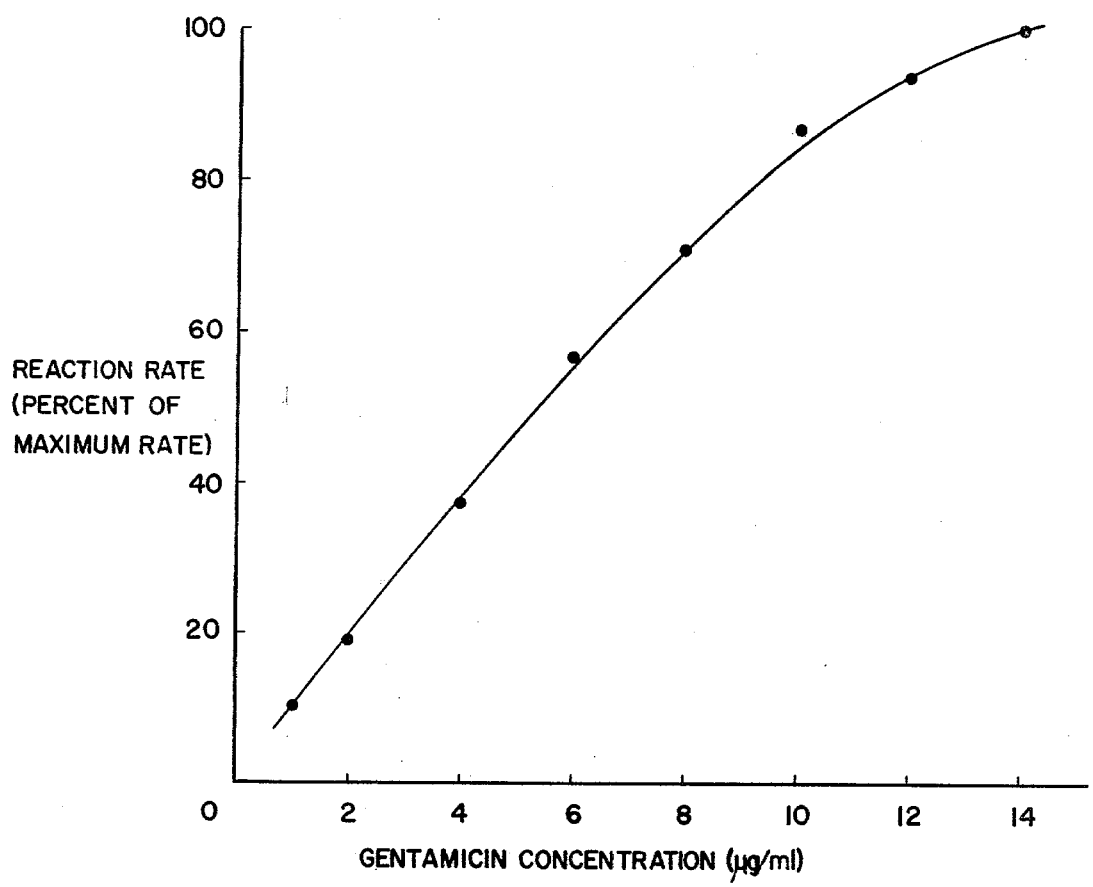
FIG. 3 is a graphical representation of the relation between gentamicin concentration and reaction rate as determined using standards as described in Example 1 for use as a standard curve in a rate assay for gentamicin.

For the standard curve, gentamicin standards were prepared from 0 to 14 μg/ml (mg/liter) in normal human serum and assayed as described in part B above. FIG. 3 of the drawings shows the standard curve of the reaction rate related to gentamicin concentration in serum standards. Reaction rate was calculated for each standard as the percentage of the maximum reaction rate in the absence of antiserum, after substraction of fluorescence in the absence of drug in the standard. No difference was observed for standards prepared in buffer compared to standards prepared in serum. Varying the time of incubation of the standards with the antibody/enzyme reagent from 0.25 to 60 minutes before adding the labeled conjugate did not alter the standard curve. Hence, the assay can be performed as rapidly as the reagents can be mixed.

D. Assay Procedure—Fixed-Time Assay

A reagent was prepared by adding 140 μl of antiserum to gentamicin (prepared as in part B above—to inhibit the maximum reaction rate in the final reagent by 75%) to 40 milliliter (ml) of 0.05 M Bicine buffer, pH 8.2. To 2.0 μl aliquots of this reagent in a cuvette were added 7.5 μl aliquots of serum standards. After mixing, 40 μl of an aqueous solution of the labeled conjugate prepared in part A (0.013 $A_{345}$ units per ml) were added to each cuvette. After further mixing, 30 μl of β-galactosidase solution (21 U/μl) were added to each cuvette and the solutions again mixed. After 20 minutes at room temperature, the resulting fluorescence for each cuvette was measured in the fluorometer and expressed in terms of the instrument reading.

E. Results—Fixed-Time Assay

Figure 4:
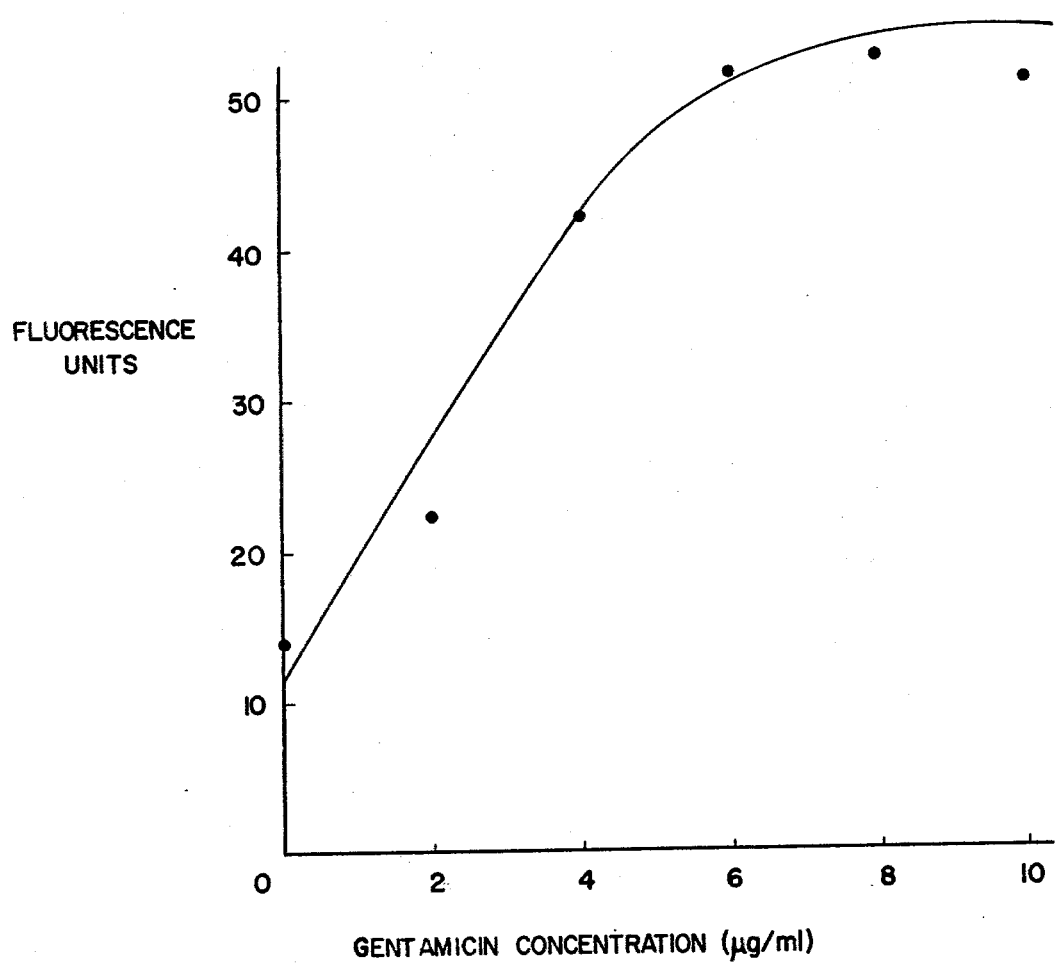
FIG. 4 is a graphical representation of the relation between gentamicin concentration and fluorescence intensity as determined using standards as described in Example 1 for use as a standard curve in a fixed-time assay for gentamicin.

A standard curve generated by testing various standard samples containing known concentrations of gentamicin according to the preceding method is depicted in FIG. 4 of the drawings.

EXAMPLE 2

Sisomicin Assay

A. Preparation of glycone-dye-drug conjugate

The labeled conjugate used in this Example was that prepared according to part A of Example 1.

B. Assay Procedure

A reagent was prepared by adding 170 μl of antiserum to gentamicin (prepared as in part B of Example 1—to inhibit the maximum reaction rate in the final reagent by 90%) and 150 μl of 0.1 mg/ml β-galactosidase (6U) to 200 ml of 50 mM Bicine buffer. To 2.0 ml aliquots of this reagent in a cuvette were added 20 μl aliquots of aqueous standard sisomicin solutions. After mixing, 20 μl of an aqueous solution of the labeled conjugate (part A above—0.032 $A_{345}$ units per ml) were added to each cuvette. Fluorescence was measured in an Aminco-Bowman Spectrofluorometer and reaction rates calculated for each standard as in part C of Example 1.

C. Results

Figure 5:
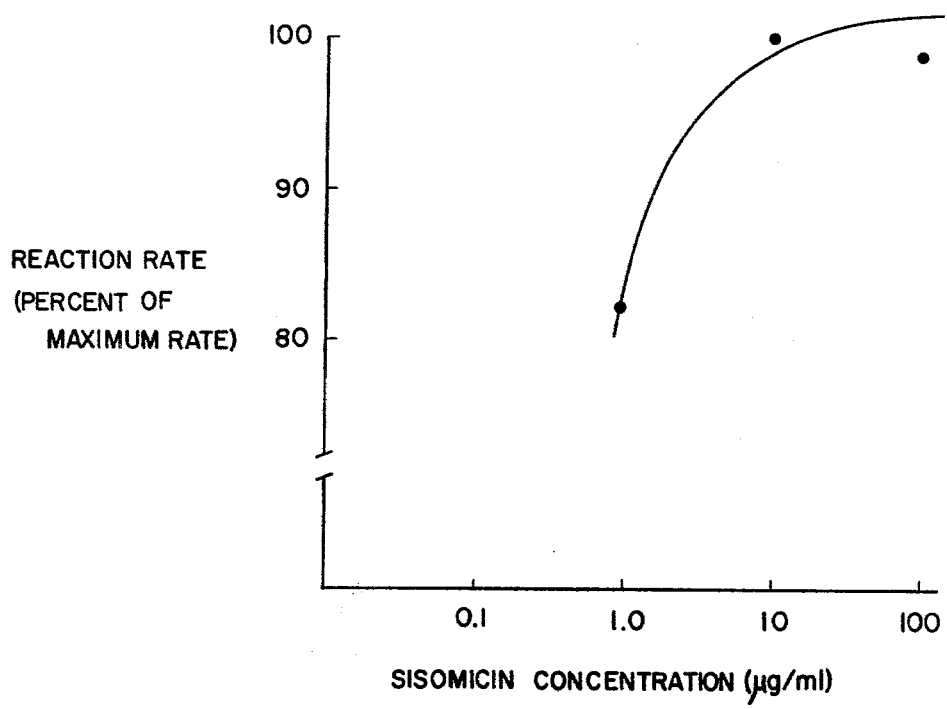
FIGS. 5 through 9 are graphical representations of the relations between the concentration of various aminoglycoside antibiotics and reaction rates as determined using standards as described in Examples 2 through 6, respectively.

A standard curve generated by testing various standard samples of sisomicin according to the preceding method is depicted in FIG. 5 of the drawings.

EXAMPLE 3

Netilmicin Assay

A. Preparation of glycone-dye-drug conjugate

The labeled conjugate used in this Example was that prepared according to part A of Example 1.

B. Assay Procedure

The procedure was the same as that described in part B of Example 2 using aqueous netilmicin standards.

C. Results

Figure 6:
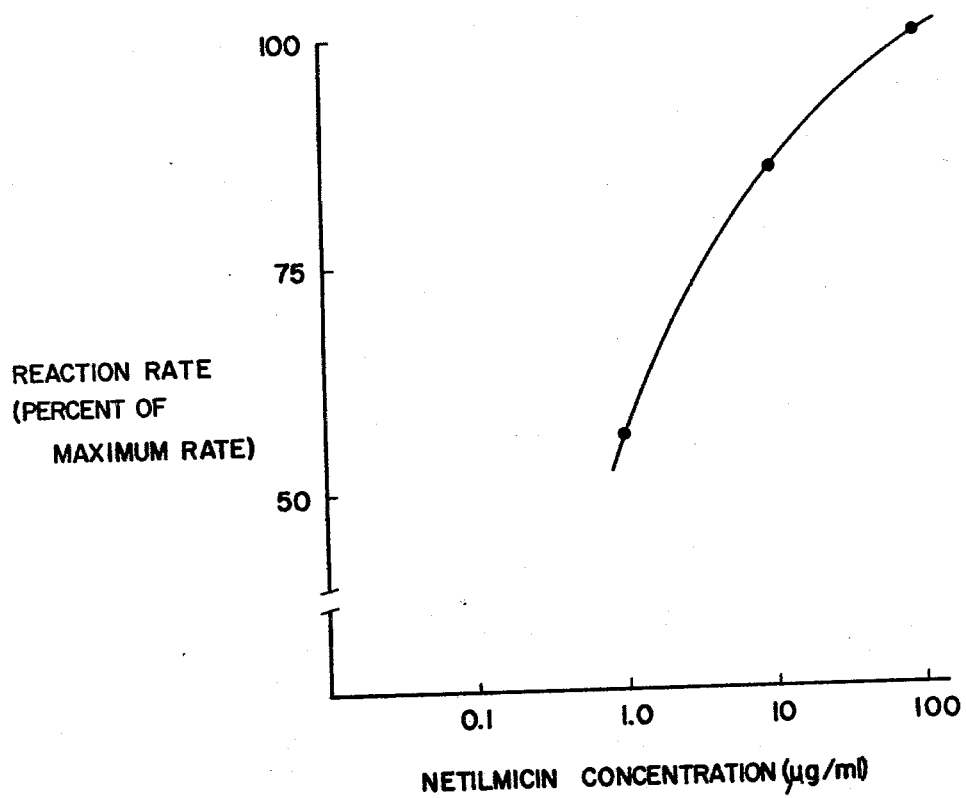

A standard curve generated for the assay of netilmicin according to the above procedure is depicted in FIG. 6 of the drawings.

EXAMPLE 4

Tobramycin Assay

A. Preparation of glycone-dye-drug conjugate

The reaction sequence and methodology for the preparation of the labeled tobramycin conjugate were basically those of Table 3 and part A of Example 1, respectively.

With 55 mg (135 μmol) of the potassium salt of β-[7-(3-carboxycoumarinoxy)]-D-galactoside was mixed 150 mg (220 μmol) of tobramycin (Eli Lilly & Co., Indianapolis, Indiana U.S.A.) in 1.5 ml of distilled water. The pH was adjusted to 3.65 by the dropwise addition of 1 N hydrochloric acid and the resulting solution cooled in an ice bath. To initiate the coupling reaction, 30 mg (160 μmol) of 1-ethyl-3(3-dimethylaminopropyl) carbodiimide hydrochloride were added. After overnight incubation of 4° C., two drops of 1 N sodium hydroxide were added to give a pH of 6.1.

The product was purified by chromatography on carboxymethyl Sephadex gel (Pharmacia Laboratories, Inc.) with ammonium formate as eluant. After an initial wash with 0.05 M ammonium formate to remove unreacted galactoside, 1.5 M ammonium formate was used to elute conjugated products. Five peaks of material absorbing at 345 nm were eluted, with the third peak being selected for use in this study.

B. Assay Procedure

A reagent was prepared by adding 150 μl of antiserum to tobramycin (prepared as described in part B of Example 1 using tobramycin in place of gentamicin in synthesis of the immunogen—to inhibit the maximum reaction rate in the final reagent by 80%) and 250 μl of an aqueous solution of β-galactosidase (4U/ml) to 100 ml of 0.05 M Bicine buffer, pH 8.2. To 2.0 ml aliquots of this reagent in a cuvette were added 10 μl aliquots of aqueous standard tobramycin solutions followed by 20 μl of an aqueous solution of the labeled conjugate prepared as in part A (0.03 $A_{345}$ units per ml). After measuring the rate of resulting fluorescence, reaction rates were calculated for each standard as in part C of Example 1.

C. Results

Figure 7:
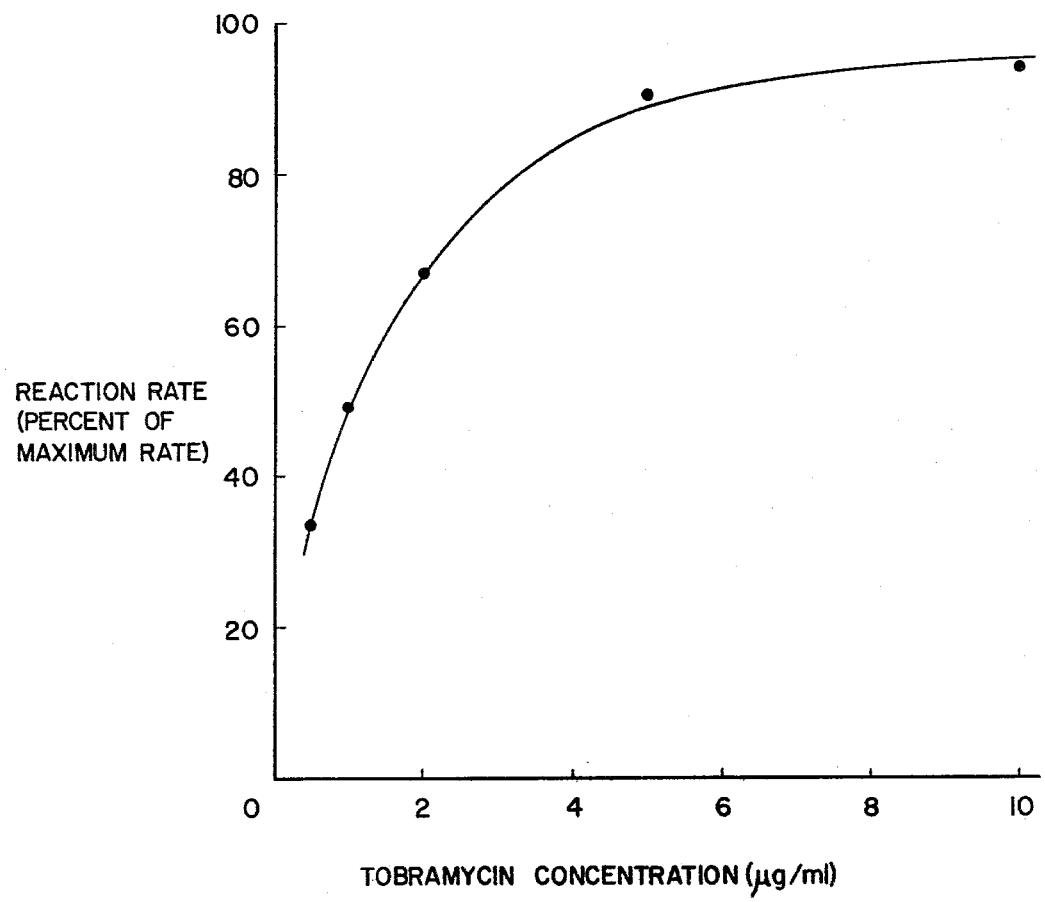

A standard curve generated by testing various tobramycin standard samples according to the preceding method is depicted in FIG. 7 of the drawings.

EXAMPLE 5

Kanamycin Assay

A. Preparation of glycone-dye-drug conjugate

The labeled conjugate used in this Example was that prepared according to part A of Example 4.

B. Assay Procedure

The procedure was the same as that described in part B of Example 4 using aqueous kanamycin standards.

C. Results

Figure 8:
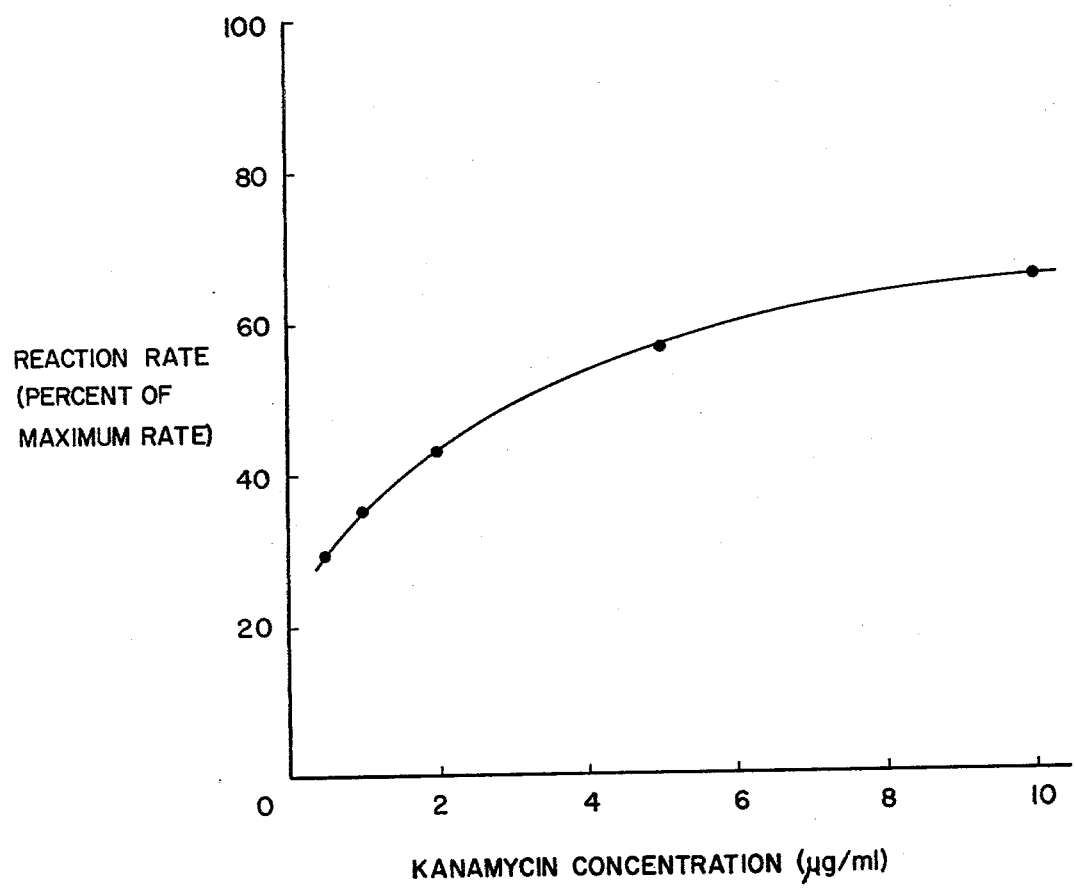

A standard curve generated for the assay of kanamycin according to the above procedure is depicted in FIG. 8 of the drawings.

EXAMPLE 6

Amikacin Assay

A. Preparation of glycone-dye-drug conjugate

The reaction sequence and methodology for the preparation of the labeled amikacin conjugate were basically those of Table 3 and part A of Example 1, respectively.

290 mg (540 μmol) of amikacin (Bristol Laboratories, Syracuse, N.Y. U.S.A.) were mixed 110 mg (270 μmol) of the potassium salt of β-[7-(3-carboxycoumarinoxy)]-D-galactoside in 3 ml of distilled water. The pH was adjusted to 4.1 by addition of 1 N hydrochloric acid. After the solution had been cooled in an ice bath, 55 mg (292 μmol) of 1-ethyl-3(3-dimethylaminopropyl) carbodiimide hydrochloride were added to initiate the reaction. After overnight incubation at 4° C., the reaction mixture was chromatographed on carboxymethyl Sephadex gel. After washing the column with 0.05 M ammonium formate to remove unreacted galactoside, 1.5 M ammonium formate was used to elute the desired conjugate. Three peaks of material absorbing at 345 nm were obtained, with the last peak being used for this study.

B. Assay Procedure

A reagent was prepared by adding 80 μl of antiserum to amikacin (prepared as described in part B of Example 1 using amikacin in place of gentamicin in synthesis of the immunogen— to inhibit the maximum reaction rate in the final reagent by 70%) and 60 μl of an aqueous solution of β-galactosidase (4 U/ml) to 60 ml of 0.05 M Bicine buffer, pH 8.2. To 2.0 ml aliquots of this reagent in a cuvette were added 10 μl aliquots of aqueous amikacin standard solutions followed by 20 μl of an aqueous solution of the labeled conjugate prepared as in part A (0.03 $A_{345}$ units per ml). After measuring the rate of resulting fluorescence, reaction rates were calculated for each standard as in part C of Example 1.

C. Results

Figure 9:
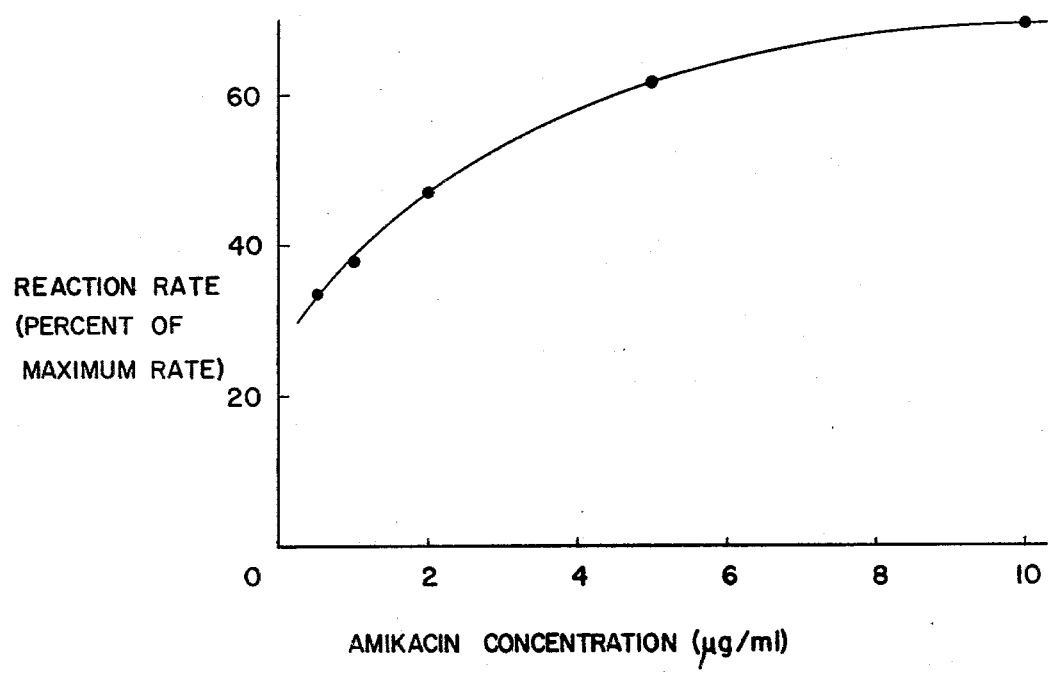

A standard curve generated by testing various amikacin standard samples according to the preceding method is depicted in FIG. 9 of the drawings.

EXAMPLE 7

Diphenylhydantion Assay

A. Preparation of glycone-dye-drug conjugate

In a liter, 3-neck round bottom flask was placed 8.64 g of a 50% suspension of sodium hydride (NaH) in mineral oil (0.18 mol). The NaH was washed free of mineral oil with hexane under an argon atmosphere. It was then suspended in 350 ml of dry dimethylformamide (DMF) and stirred while a solution of 34.4 g (0.173 mol) of N-(4-bromobutyl)phthalimide in 150 ml of dry DMF was added over a 20 minute period. After stirring at room temperature for 18 hours, the reaction was diluted with 200 ml of $H_2O$ and the precipitate collected and dried to yield 49 g of 2-[(4N-phthalimido)butoxy]-benzophenone, mp 119°–121° C. A 1 g sample was recrystallized from ethanol to give 740 mg of white needles, mp 121°–122° C.

A mixture of 22.4 g (0.056 mol) of 2-[(4-N-phthalimido)butoxylbenzophenone, 4.15 g (0.064 mol) of potassium cyanide, 17.3 g (0.18 mol) of ammonium carbonate, 24 ml of water, and 200 ml of DMF was placed in a steel autoclave and heated at 110° C. for 4 days. The contents were cooled and adsorbed onto 100 g of silica gel 60 and placed atop a 700 g column of silica gel made up in 9:1 (v:v) carbontetrachloride:acetone. Elution was with the same solvent and fractions of approximately 20 ml volumes were collected. Fractions 276–803 were combined and evaporated to give 4.65 g of solid. Recrystallization from ethanol gave 2.65 of 5-[2-(4-N-formylamino)butoxyphenyl]-5-phenylhydantoin as a white solid, mp 201°–203° C.

A solution of 3.5 g (9.4 mmol) of 5-[2-(4-N-formylamino)butoxyphenyl]-5-phenylhydantoin in 100 ml of 1 N sodium hydroxide was heated on the steam bath for 24 hours. The solution was cooled and neutralized with carbondioxide until precipitation ceased. The precipitate was filtered and recrystallized twice; first from pyridine-2-propanol, then from methanol to give 1.5 g of 5-[2-(4-aminobutoxy)phenyl]-4-phenylhydantoin as fine white crystals, mp 235° C. (decomp).

A mixture of 808 mg (2 mmol) of the potassium salt of 7-β-galactosylcoumarin-3-carboxylic acid [Burd et al, Clin. Chem. 23:1402(1977)] and 20 ml of dry DMF was made and cooled to 0° C. To this mixture was added 216 mg (2 mmol) of ethylchloroformate. After stirring for one hour at this temperature, 638 mg (2 mmol) of 5-[2-(4-aminobutoxy)phenyl]-5-phenylhydantoin, 244 mg of 4-dimethylaminopyridine, and 5 ml of dry pyridine were added. After stirring for 5 hours, the reaction was stored overnight at 0° C., then adsorbed onto 7 g of silica gel 60. The impregnated silica gel was placed atop a column of 200 g of silica gel 60 and the column eluted with a gradient of 2 liters of ethyl acetate to 2 liters of 1:1 (v:v) ethylacetate:ethanol. Ten ml fractions were collected. Fractions 143–160 were combined to give approximately 200 mg of the labeled conjugate N-{4-[2-(5-phenylhydantoinyl-5)phenoxy]butyl}-7-β-galactosylcoumarin-3-carboxamide as a glossy solid.

The solid was taken up in methanol and chromatographed on Sephadex LH-20 (45 cm by 3.2 cm), eluting with methanol. Seven ml fractions were collected. Fractions 30 to 40 were combined and evaporated to give 100 mg of the desired labeled conjugate as a pale, glossy solid.

Analysis: Calculated for $C_{35}H_{35}N_3O_{12} \cdot H_2O$: C, 59.40; H, 5.24; N, 4.95. Found: C, 59.51; H, 5.04; N, 6.14. $[\alpha]_D = -39.04$ (c 1.0, methanol).

B. Assay Procedure

A reagent was prepared containing β-galactosidase (0.018 U/ml) and antiserum to diphenylhydantoin (raised against o-caproyldiphenylhydantoin—in an amount sufficient in the final reagent to decrease fluorescence to 10% of that observed in the absence of antibody) in 50 mmolar Bicine buffer, pH 8.2. To 3.0 ml aliquots of this reagent in a cuvette were added 100 μl aliquots of diphenylhydantoin serum standards followed by 100 μl aliquots of the labeled conjugate (part A above). After mixing, the reaction mixtures were incubated 20 minutes at room temperature and fluorescence measured in each cuvette (excitation and emission wavelengths were 400 and 450 nm, respectively).

C. Results

Figure 10:
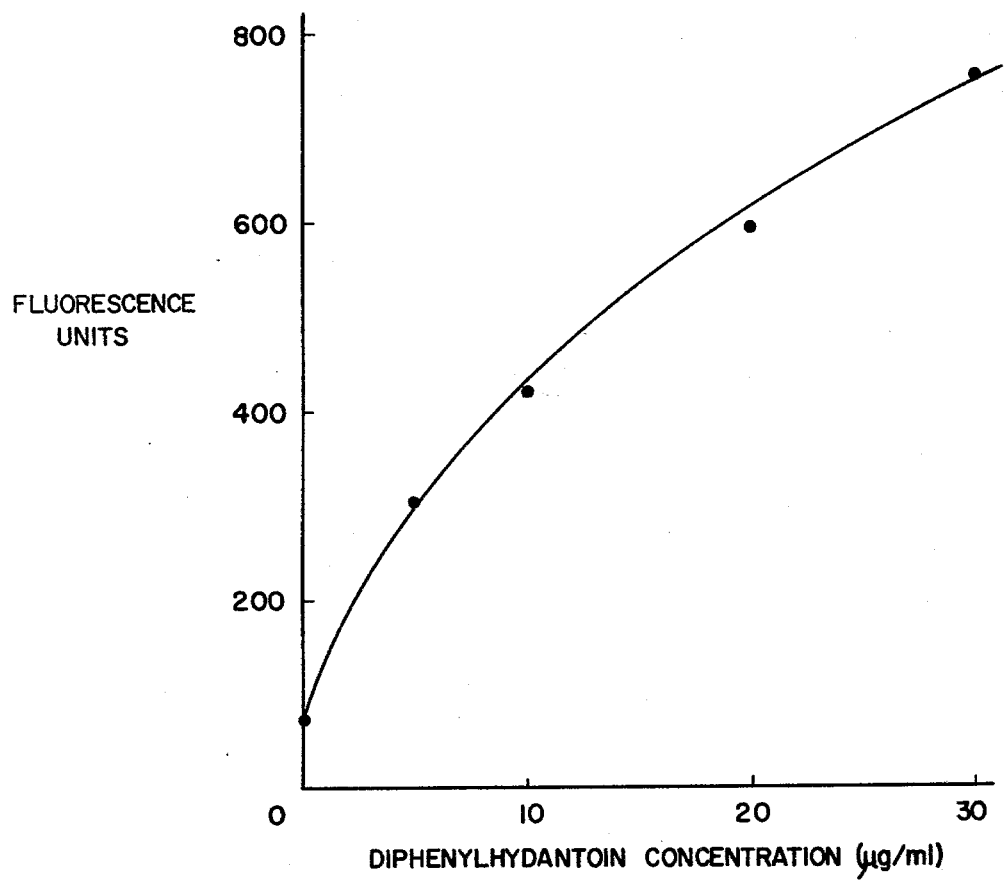
FIG. 10 is a graphical representation of the relation between the concentration of diphenylhydantoin and fluorescence intensity as determined using standards as described in Example 7 for use as a standard curve in a fixed-time assay for diphenylhydantoin.

A standard curve generated for the assay of diphenylhydantoin according to the above procedure is depicted in FIG. 10 of the drawings.

The examples demonstrate that the use of the novel labels of the present invention are more advantageous than the prior labels used in specific binding assays employing an enzyme-cleavable substrate as label. With the present labels, endogeneous enzyme activity of a serum sample and antibody-induced hydrolysis of the cleavable linkage were found not to be a source of potential error. Further, no background hydrolysis of the labeled conjugate was observed.

What is claimed is:

1. A β-galactosyl-umbelliferone-labeled aminoglycoside antibiotic conjugate of the formula:

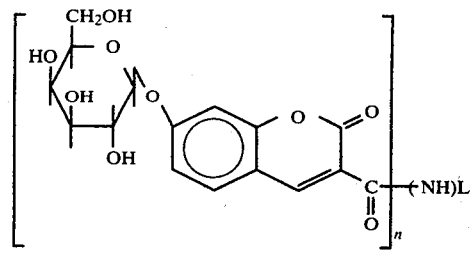

wherein —NH)L is an aminoglycoside antibiotic selected from gentamicin, tobramycin, amikacin, kanamycin, sisomicin, or netilmicin bound through an amino group thereof by an amide bond and n equals 1 to the total number of primary amino groups in the selected antibiotic, inclusive.

2. The conjugate of claim 1 wherein L is gentamicin.
3. The conjugate of claim 1 wherein L is tobramycin.
4. The conjugate of claim 1 wherein L is amikacin.
5. The conjugate of claim 1 wherein L is kanamycin.
6. The conjugate of claim 1 wherein L is sisomicin.
7. The conjugate of claim 1 wherein L is netilmicin.
8. A compound of the formula:

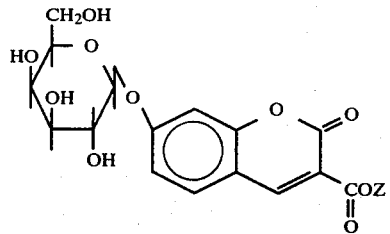

wherein Z is hydrogen, potassium or sodium.

9. The compound of claim 8 wherein Z is potassium.
10. The compound of claim 8 wherein Z is sodium.
11. The compound of claim 8 wherein Z is hydrogen.

* * * * *